US008298521B2

(12) United States Patent
Schwartz et al.

(10) Patent No.: US 8,298,521 B2
(45) Date of Patent: *Oct. 30, 2012

(54) TREATMENT FOR EYE DISORDER

(75) Inventors: Daniel M. Schwartz, San Francisco, CA (US); Scott Fraser, Lacanada-flintridge, CA (US); Robert H. Grubbs, South Pasadena, CA (US); Justin P. Gallivan, Atlanta, GA (US); Changjun Yu, Pasadena, CA (US)

(73) Assignees: The Regents of the University of California, Oakland, CA (US); California Institute of Technology, Pasadena, CA (US)

( * ) Notice: Subject to any disclaimer, the term of this patent is extended or adjusted under 35 U.S.C. 154(b) by 1138 days.

This patent is subject to a terminal disclaimer.

(21) Appl. No.: 12/126,100

(22) Filed: May 23, 2008

(65) Prior Publication Data

US 2008/0286255 A1    Nov. 20, 2008

Related U.S. Application Data

(63) Continuation of application No. 10/611,013, filed on Jul. 1, 2003, now Pat. No. 7,381,404.

(60) Provisional application No. 60/393,505, filed on Jul. 2, 2002.

(51) Int. Cl.
*A61K 31/74* (2006.01)

(52) U.S. Cl. ......... 424/78.04; 424/78.02; 607/1; 607/88

(58) Field of Classification Search ........................ None
See application file for complete search history.

(56) References Cited

U.S. PATENT DOCUMENTS

| | | | | |
|---|---|---|---|---|
| 4,944,944 A * | 7/1990 | Tang et al. | ..................... | 424/94.6 |
| 5,310,764 A | 5/1994 | Baranowitz et al. | .......... | 614/725 |
| 5,410,016 A | 4/1995 | Hubbell et al. | ................ | 528/354 |
| 5,462,990 A | 10/1995 | Hubbell et al. | .............. | 525/54.1 |
| 5,468,505 A | 11/1995 | Hubbell et al. | ................ | 424/484 |
| 5,567,435 A | 10/1996 | Hubbell et al. | ................ | 424/426 |
| 5,573,934 A | 11/1996 | Hubbell et al. | ................ | 435/177 |
| 5,626,863 A | 5/1997 | Hubbell et al. | ................ | 424/426 |
| 5,756,541 A | 5/1998 | Strong et al. | ................... | 514/502 |
| 5,798,349 A | 8/1998 | Levy et al. | ..................... | 514/185 |
| 5,844,016 A | 12/1998 | Sawhney et al. | ................ | 522/13 |
| 5,858,746 A | 1/1999 | Hubbell et al. | ................ | 435/177 |
| 5,910,510 A | 6/1999 | Strong et al. | ................... | 514/502 |
| 5,935,942 A | 8/1999 | Zeimer | ........................... | 514/63 |
| 5,986,043 A | 11/1999 | Hubbell et al. | ................ | 528/354 |
| 6,059,828 A | 5/2000 | Peyman | .......................... | 623/4.1 |
| 6,060,582 A | 5/2000 | Hubbell et al. | ................ | 528/354 |
| 6,121,341 A | 9/2000 | Sawhney et al. | ................ | 522/84 |
| 6,128,525 A | 10/2000 | Zeng et al. | ..................... | 600/746 |
| 6,140,314 A | 10/2000 | Zeimer | ........................... | 514/63 |
| 6,149,931 A | 11/2000 | Schwartz et al. | ............. | 424/427 |
| 6,153,211 A | 11/2000 | Hubbell et al. | ................ | 424/426 |
| 6,225,303 B1 | 5/2001 | Miller et al. | ................... | 514/185 |
| 6,248,727 B1 | 6/2001 | Zeimer | ........................... | 514/63 |
| 6,267,954 B1 | 7/2001 | Abitol et al. | ................... | 424/93.7 |
| 6,271,233 B1 | 8/2001 | Brazzell et al. | ................ | 514/249 |
| 6,306,922 B1 | 10/2001 | Hubbell et al. | .................. | 522/71 |
| 6,371,615 B1 | 4/2002 | Schweitzer et al. | .......... | 351/221 |
| 6,387,977 B1 | 5/2002 | Sawhney et al. | ............... | 522/184 |
| 6,461,640 B1 | 10/2002 | Hubbell et al. | ................ | 424/486 |
| 6,465,001 B1 | 10/2002 | Hubbell et al. | ................ | 435/174 |
| 6,475,508 B1 | 11/2002 | Schwartz et al. | ............. | 424/427 |
| 6,602,975 B2 | 8/2003 | Hubbell et al. | ................ | 528/354 |
| 6,632,446 B1 | 10/2003 | Hubbell et al. | ................ | 435/423 |
| 6,703,037 B1 | 3/2004 | Hubbell et al. | ................ | 424/401 |
| 6,858,229 B1 | 2/2005 | Hubbell et al. | ................ | 424/484 |
| 7,011,952 B2 | 3/2006 | Hageman et al. | .............. | 435/7.1 |
| 7,291,673 B2 | 11/2007 | Hubbell et al. | .................... | 435/6 |
| 7,381,404 B2 | 6/2008 | Schwartz et al. | .......... | 424/78.04 |
| 2002/0049247 A1 | 4/2002 | Chen | .......................... | 424/178.1 |
| 2003/0087985 A1 | 5/2003 | Hubbell et al. | ................ | 523/114 |
| 2004/0138329 A1 | 7/2004 | Hubbell et al. | ................ | 523/114 |
| 2004/0199130 A1 | 10/2004 | Chornenky et al. | ........... | 604/289 |

FOREIGN PATENT DOCUMENTS

| | | |
|---|---|---|
| WO | WO 00/31588 | 6/2000 |
| WO | WO 01/51087 | 7/2001 |
| WO | WO 03/049685 | 6/2003 |

OTHER PUBLICATIONS

Bird, "Bruch's membrane change with age," *Br. J. Ophthalmol.*, 76(3):166-8, 1992.

Downs et al., "Viscoelastic characterization of perpapillary sciera: Material properties by quadrant in rabbit and monkey eyes," *J. Biomech. Eng.*, 125:124-131, 2003.

Fisher et al., "Photoinitiated polymerization of biomaterials," *Annu. Rev. Mater. Res.*,31:171-81, 2001.

(Continued)

*Primary Examiner* — Allison Ford

(74) *Attorney, Agent, or Firm* — Rudy J. Ng; Carol L. Francis; Bozicevic, Field & Francis LLP

(57) ABSTRACT

The present invention relates to altering the physical and/or chemical properties of at least part of at least one tissue in the eye. In a specific embodiment, it relates to the treatment of any eye disorder, although in particular embodiments the individual has a thickened Bruch's membrane. An activating energy source is utilized to effect a controlled diffusion enhancement and/or degradation of Bruch's membrane that enables improved diffusional transport between the choroid and retina. The individual is administered an inactivated diffusion-enhancing molecule that becomes associated with the membrane, which is then precisely exposed to an activating energy source, such as light or ultrasound.

36 Claims, 1 Drawing Sheet

OTHER PUBLICATIONS

Gorrsch et al., "Hematogenous photosensitization: A mechanism for the development of Afe-related macular degeneration," *Investigative Ophthalmology & Visual Science*, 31(9):1674-1682, 1990.

Goss et al., "Optometric Clinical Practice Guidance: Care of the Patient with Myopia," Reference Guide for Clinicians, © American Optometric Association, 1997.

Gottsch et al., "Light-induced deposits in Bruch's membrane of protoporphyric mice," *Arch. Ophthalmol.*, 111:126-129, 1993.

Green et al., "Pathologic features of senile macular degeneration," *Ophthalmology*, 92(5):615-627, 1985.

Haigis et al., "Comparison of immersion ultrasound biometry and partial coherence interferometry for introcular lens calculation according to Haigis," *Graef's Arch. Clin. Exp. Ophthalmol*, 238:765-773, 2000.

Holz et al., "Analysis of lipid deposits extracted from human macular and peripheral Bruch's membrane," *Arch. Ophthalmol.*, 112(3):402-6, 1994.

Jin et al., "Effect of electrostatic interaction between Glycosaminoglycans on the shear stiffness of cartilage: a molecular model and experiments," *Macromolecules*, 34:8330-8339, 2001.

Kaufman, "Strengthening the corea," *Cornea*, 33(5):432-2004.

Knapp et al., "Theology of reconstituted type I collagen gel in confined compression," *J. Rheol.*, 41(5):971-993, 1997.

Mester et al., "A comparison of two different formulations of diclofenac sodium 0.1 in the treatment of inflammation following cataract-intraocular lens surgery," *Drugs R&D*, 3(3):145-151, 2002.

Moore et al., "Age-related variation in the hydraulic conducitivity of Bruch's membrane," *Invest. Ophthalmol. Vis. Sci.*, 36(7):1290-7, 1995.

Noecker, "Effects of common ophthalmic preservatives on ocular health," *Advances in Therapy*, 18(5):205-215, 2001.

Nowak, "Age-related macular degeneration (AMD): pathogenesis and therapy," *Pharmacol. Rep.*, 58(3):353-63, 2006.

Office Communication, issued in U.S. Appl. No. 10/611,013, dated Jan. 6, 2005.

Office Communication, issued in U.S. Appl. No. 10/611,013, dated Apr. 28, 2005.

Office Communication, issued in U.S. Appl. No. 10/611,013, dated Jul. 26, 2005.

Office Communication, issued in U.S. Appl. No. 10/611,013, dated Nov. 2, 2005.

Office Communication, issued in U.S. Appl. No. 10/611,013, dated Jul. 19, 2006.

Office Communication, issued in U.S. Appl. No. 10/611,013, dated Apr. 19, 2007.

Puliafito et al., "Imaging of macular diseases with optical coherence tomography," *Ophthalmology*, 102(2):217-229, 1995.

Rather et al., "Biomaterials: Where we have been and where we are going," *Annu. Rev. Biomed. Eng.*, 6:41-75, 2004.

Ruberti et al., "Quick-freeze/deep-etch visualization of age-related lipid accumulation in Bruch's membrane," *Invest. Ophthalmol. Vis. Sci.*, 44(4):1753-9, 2003.

Sheraidah et al., "Correlation between lipids extracted from Cruch's membrane and age," *Ophthalmology*, 100(1):47-51, 1993 (Abstract Only).

Spaide et al., "Characterization of peroxidized lipids in Bruch's membrane," *Retina*, 19(2):141-7, 1999. (Abstract only).

Spoert et al., "Induction of cross-links in corneal tissue," *Exp. Eye Res.*, 66:97-103, 1998.

St. Helen et al., "Rheology of the human sciera, 1 anelastic behavior," *Am. J. Ophthalmol.*, 52:539-48, 1961.

Tezel et al., "Reengineering of aged Bruch's membrane to enchance retinal pigment epithelium repopulation," *Invest. Opth. Vs. Sci.*, 45:3337-3348, 2004.

Tezel et al., "Regeneration of the inner collagenous layer (1CL) of human Bruch's membrane by cleaning and extracellular matrix protein coating: Morphometic evidence," *Investigative Ophth. & Visual Science*, 44:1-2, 2003.

Van Hest et al., "Protein-based materials, towards a new level of structural control," *Chem. Commun.*, 1897-1904, 2001.

Visudyne—Overview: Veterporfin for Injection, available online at http://www.visudyne.com, May 2002.

Wollensak et al., "Riboflavin/ultraviolet-A-induced collagen crosslinking for the treatment of keratocous," *Am. J. Ophthalmol.*, 135:620-627, 2003.

\* cited by examiner

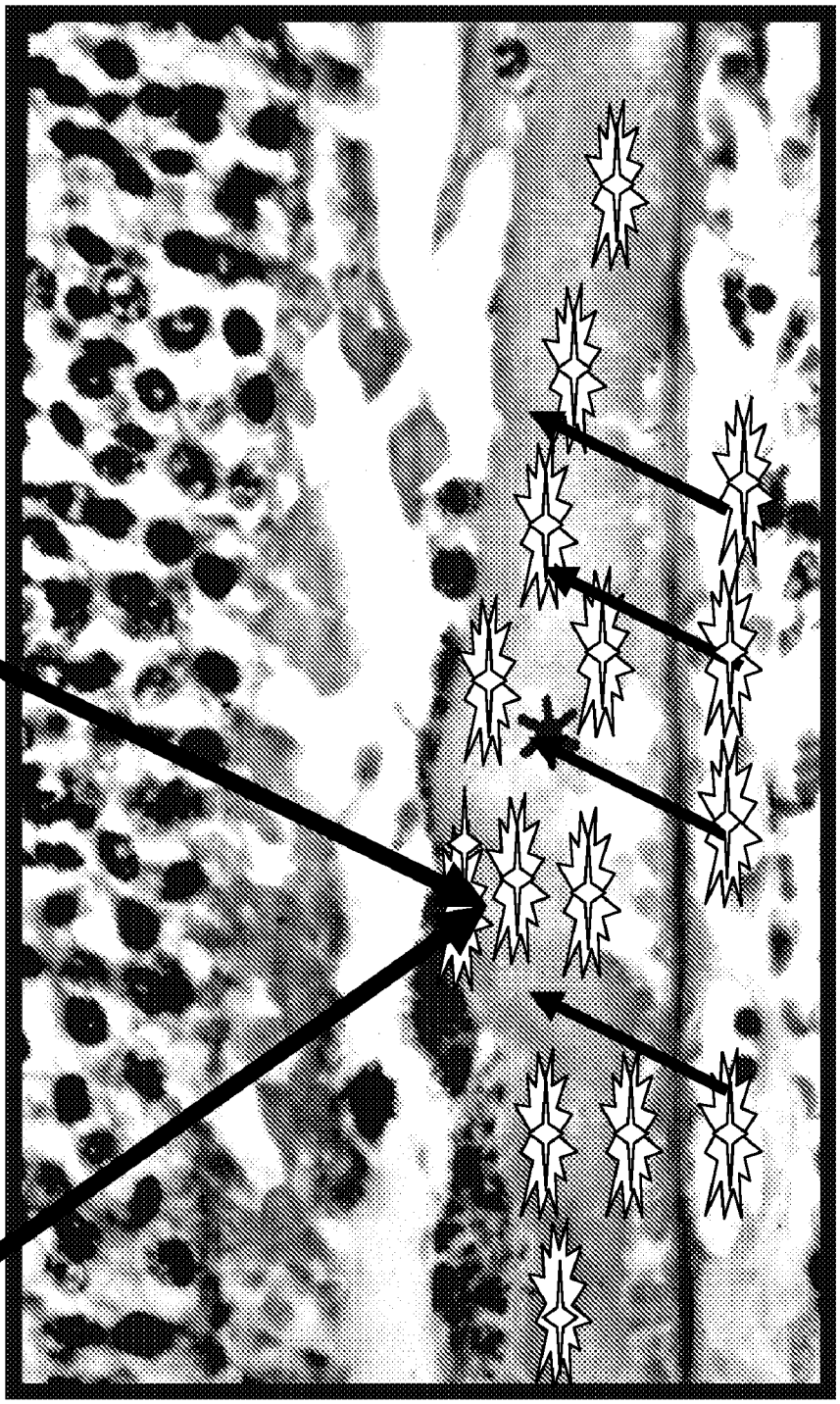

TREATMENT FOR EYE DISORDER

The present invention claims priority under 35 U.S.C. 120 to U.S. Utility application Ser. No. 10/611,013 filed 1 Jul. 2003 which claims the benefit of U.S. Provisional Patent Application Ser. No. 60/393,505, filed Jul. 2, 2002, pursuant to 35 U.S.C. 119(e). The contents of these priority documents are incorporated by reference herein in their entirety.

FIELD OF THE INVENTION

The present invention is generally directed to the fields of opthalmology and cell biology. Specifically, it relates to altering the physical and/or chemical properties of an ocular tissue. More specifically, it describes a means to detect and/or reduce the thickening and/or change the permeability of Bruch's membrane associated with eye disorders, such as macular degeneration. Even more specifically, it regards administration of an inactivated diffusion-enhancing molecule to Bruch's membrane followed by activation of the diffusion-enhancing molecule through an energy source.

BACKGROUND OF THE INVENTION

Age related macular degeneration (AMD) is a progressive eye condition affecting as many as 10 million Americans. AMD is the number one cause of vision loss and legal blindness in adults over 60 in the U.S. As the population ages, and the "baby boomers" advance into their 60's and 70's, a virtual epidemic of AMD will be prevalent. The disease affects the macula of the eye, where the sharpest central vision occurs. Although it rarely results in complete blindness, it robs the individual of all but the outermost, peripheral vision, leaving only dim images or black holes at the center of vision.

Macular degeneration is categorized as either dry (atrophic) or wet (neovascular). The dry form is more common than the wet, with about 90% of AMD patients diagnosed with dry AMD. The wet form of the disease usually leads to more serious vision loss.

In the dry form, there is a breakdown or thinning of the retinal pigment epithelial cells (RPE) in the macula, hence the term "atrophy". These RPE cells are important to the function of the retina, as they metabolically support the overlying photoreceptors.

The clinical hallmark of atrophic AMD is accumulation of macular drusen, yellowish deposits just deep to the retinal pigment epithelium ("RPE"). Histopathologic examination of eyes with atrophic AMD reveals deposition of lipid and proteinaceous material deep to the RPE in Bruch's membrane. In aged eyes with AMD, Bruch's membrane is often about 3 times thicker than normal. This thickening is thought to be comprised of lipid as well as modified and cross-linked protein, which impedes transport of nutrients across Bruch's membrane from the choriocapillaris to the outer retina This thickened barrier comprised of lipid and cross-linked protein impedes transport of nutrients across Bruch's membrane from the choriocapillaris to the outer retina. At present, there is no proven effective treatment for dry AMD other than the use of multivitamins and micronutrients.

Wet AMD occurs when new vessels form and grow through Bruch's membrane into the sub-RPE and subretinal space. This neovascular tissue is very fragile and hyperpermeable. Frequently, it bleeds causing damage to the overlying retina. As the blood organizes, functional macular tissue is replaced by scar tissue. To prevent visual loss, it would be desirable to intervene therapeutically prior to the development of neovascularization.

Although the exact etiology of AMD is not known, several risk factors seem to be important. For example, ARMD may be caused by chronic exposure of the retina to light. The presence or absence of certain nutrients in the diet, such as the antioxidant vitamins E and C, also may affect one's predisposition for ARMD. Other conditions, such as hypertension and smoking, are also considered to be important risk factors for the development of this disease.

AMD is a challenging disease for both patient and doctor, because there are very few treatment options and, with the exception of anti-oxidants, no proven preventative therapy. While some individuals experience only minor inconvenience from macular degeneration, many others with more severe forms of macular degeneration are incapacitated. Current therapies, including laser photocoagulation, photodynamic therapy, and anti-angiogenic therapeutics have had mixed results, and, in certain instances, have caused deleterious side effects. A need therefore exists for a treatment that reduces or limits the effects of macular degeneration.

Laser photocoagulation is effective in clinical trials, but only a minority of patients with AMD are good candidates for treatment. Furthermore, even after successful ablation of choroidal neovascularization with laser treatment recurrent neovascular tissue grows frequently. Visudyne® (Novartis Ophthalmics; Duluth, Ga.), a photodynamic therapy or PDT, uses light-activated drugs to potentially halt or slow abnormal cell growth. The therapy treats late stages of disease, characterized by choroidal neovascularization. Briefly, a photosensitizer is administered intravenously and attaches to lipoprotein receptors, particularly found in cells undergoing rapid proliferation. Shortly after administration, the compound is activated with a pre-calculated dose of light at a particular wavelength, resulting in conversion of normal oxygen to free radical singlet oxygen, which in turn causes closure of neovascular tissue. The therapy, in specific embodiments, treats the blood vessel proliferation. However, because the underlying cause of macular degeneration is not addressed by treatment of choroidal neovascularization with photodynamic therapy, recurrent neovascularization occurs commonly within several months after treatment.

U.S. Pat. No. 5,756,541 is directed to methods to improve visual acuity including administering a photoactive compound in an amount sufficient to localize to a target ocular tissue and irradiating the target tissue with light from a laser, wherein the wavelength of radiation is absorbed by the photoactive compound and the radiation is conducted for a time and at an intensity sufficient to improve visual acuity. In specific embodiments, the photoactive compound is a green porphyrin. U.S. Pat. No. 5,910,510 is directed to an identical method having a particular irradiation timing.

U.S. Pat. No. 5,798,349 regards methods to treat conditions of the eye characterized by unwanted neovasculature, such as AMD, by administering a liposomal formulation of a green porphyrin in an amount and time sufficient to localize in the neovasculature, followed by irradiation of the neovasculature with laser light, wherein the light absorbed by the green porphyrin occludes the neovasculature. In the related U.S. Pat. No. 6,225,303, the irradiance is in a range from about 300 mW/cm$^2$ to about 900 mW/cm$^2$.

U.S. Pat. No. 6,128,525 is directed to method and apparatus controlling dosimetry of photodynamic therapy.

U.S. Pat. No. 5,935,942 regards methods of occluding vasculature in a mammalian eye including co-administering intravenously a fluorescent dye encapsulated with heat-sensitive liposomes and a tissue-reactive agent activated by irradiation. The liposomes are heated in the eye to release their contents, wherein the tissue-reactive agent remains inactive, followed by monitoring of fluorescent dye flow within the vasculature. The tissue-reactive agent is activated in the vasculature having subnormal blood flow, such that the activated agent chemically occludes the vasculature. The related U.S. Pat. No. 6,140,314 methods further comprise coadministration of a tissue-specific factor effective to impair growth or regeneration of a blood vessel. The related U.S. Pat. No. 6,248,727 regards related diagnostic reagents and kits.

Thus, although alternative methods for eye disorders exist, the present invention addresses a need in the art for therapy for the disorder prior to the point of, for example, neovascularization of the eye tissue, particularly in reversing the pathology of a tissue, such as Bruch's membrane, associated with the eye disorder.

SUMMARY OF THE INVENTION

The present invention regards methods and compositions for altering physical and/or chemical properties of an ocular tissue. In specific embodiments, it refers to enhancement of diffusion through or across a tissue, targeted destruction of cells, and/or targeted alteration of at least part of at least one ocular tissue in an individual. This may be accomplished, in particular embodiments, using a means to effect a controlled enhancement of diffusion and/or other controlled alteration, such as with light or ultrasound. Some aspects of the present invention are directed to treating eye disorders at early stages, and a skilled artisan will recognize the utility of this invention for such a purpose.

In a specific, yet only exemplary, embodiment of the present invention, Bruch's membrane is the targeted tissue. With aging and especially in macular degeneration, Bruch's membrane develops a lipid and cross-linked protein barrier. Impaired diffusion across Bruch's membrane in patients with macular degeneration, promotes release of angiogenic factors by the nutritionally deprived retina. This, in turn, causes growth of neovascular tissue through Bruch's membrane with subsequent bleeding, leakage of serous fluid, and severe visual loss. Some aspects of the present invention allow treatment/administration before or shortly after choroidal neovascularization develops.

To improve diffusion across Bruch's membrane and prevent development of visual loss, it is desirable to alter the physicochemical properties of a tissue associated with visual loss, such as reduce the lipid and cross-linked protein barrier that accumulates in Bruch's membrane with aging and in patients with AMD. This invention is directed to means and compositions to accomplish this using light or ultrasound to effect a controlled enhancement of diffusion and/or partial degradation of Bruch's membrane that enables improved diffusional transport between the choroid and the retina. Energy (exemplary forms being light or ultrasound) is utilized to achieve selective activation of tissue-altering substances (which may also be referred to as lipid and/or protein degrading substances), because this use targets the alteration to Bruch's membrane while leaving adjacent tissues minimally affected. If active tissue-altering molecules were administered systemically, they would not be selective for Bruch's membrane but would potentially damage other tissues. To target the desired tissue (such as Bruch's membrane) specifically, the tissue-altering molecule is administered in inactive form, such as by systemic injection or ingestion, or local (intraocular, periocular) injection. In a specific embodiment, the molecule is lipophilic. It binds to multiple tissues in an inactive form before it is gradually eliminated. It is only activated by an energy source (e.g. light, ultrasound, or both) that is precisely applied to the eye to achieve preferential activation of the tissue-altering substance in Bruch's membrane. Once activated, the tissue-altering molecules alter the lipids and/or cross-linked protein in Bruch's membrane, such as to improve transmembrane diffusion. In a specific embodiment, to obtain precision in the location of activation, the photochemical activation steps comprise 2-photon photochemistry.

In an object of the present invention, there is a method of treating an eye disorder comprising the step of increasing diffusion across Bruch's membrane in said eye. In a specific embodiment, the increased diffusion is a result of reducing the thickness, altering the composition, or both, of said membrane.

In an additional object of the present invention, there is a method for increasing diffusion across Bruch's membrane in at least one eye of an individual, comprising the steps of administering to the Bruch's membrane an inactive form of a degradation molecule in an amount sufficient to form a Bruch's membrane/inactive degradation molecule complex; and exposing said complex to an activating source, wherein said activating source activates said inactive degradation molecule into an active form of said degradation molecule, said activation resulting in an increase in diffusion across said membrane. In a specific embodiment, the increase in diffusion is a result of reducing the thickness or altering the composition of said membrane. In another specific embodiment, the increase in diffusion is a result of alteration of a lipid, a cross-linked protein, or both in the membrane. In a further specific embodiment, the individual has an eye disorder, such as AMD, juvenile macular degeneration, Sorby's fundus dystrophy, or age-related decrease in visual function unrelated to macular degeneration. In a specific embodiment, the inactive degradation molecule binds directly to the membrane.

In another specific embodiment of the present invention, the inactive degradation molecule is a protein, detergent, surfactant (useful for caged cyclodextrin). In a further specific embodiment, the protein is an enzyme. In an additional specific embodiment, the inactive enzyme is further defined as being caged by the incorporation of at least one photoremovable protecting group on an amino acid sidechain of said enzyme. In a specific embodiment, the protecting group is o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl, or a combination thereof. In another specific embodiment, the protecting group is o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl or derivatives thereof. In a specific embodiment, the amino acid is cysteine, aspartate, glutamate, histidine, lysine, asparagine, glutamine, arginine, serine, threonine, tyrosine, or a combination thereof. In a specific embodiment, the detergent is further defined as being caged by a compound comprising at least one o-nitrobenzyl, desyl, phenacyl, trans-o-cinnamoyl, coumarinyl, quinoline-2-onyl, xanthenyl, thioxanthenyl, selenoxanthenyl and anthracenyl, or stilbenyl group. In another specific embodiment, the protein is further defined as being caged in an ultrasound contrast agent. In a specific embodiment, the ultrasound contrast agent is a microbubble or a liposome. In another specific embodiment, the protein further comprises a protein binding domain. In a further specific embodiment, the protein binding domain is a heterodimeric domain. In an additional specific embodiment, the protein binding domain is a leucine zipper domain, a chitin-binding domain, or a Src homology 2 (SH2) domain.

In another specific embodiment of the present invention, the inactive degradation molecule is administered to the individual in a pharmacologically acceptable composition. In another specific embodiment, the inactive degradation molecule is administered in a pharmacologically acceptable composition systemically to the individual. In an additional specific embodiment, the inactive degradation molecule is administered in a pharmacologically acceptable composition to the individual orally, by injection (such as periocular or intraocular), rectally, vaginally, or topically. In a specific embodiment, the enzyme is a matrix metalloproteinase, a cholesterol esterase, a lipase, a cathepsin, a protease, or a combination thereof. In a specific embodiment, the protease is a serine protease. In a specific embodiment, the activating source is energy. In a further specific embodiment, the energy is light or ultrasound. In an additional specific embodiment, the exposing step is further defined as exposing said complex to light energy from a focused laser source. In another specific embodiment, the degradation molecule is fluorescently labeled.

In another embodiment of the present invention, there is a method of treating age-related macular degeneration in at least one eye of an individual, said macular degeneration characterized by a thickened Bruch's membrane, comprising administering to said individual an inactivated degradation molecule in an amount sufficient for said molecule to associate with the membrane to form a Bruch's membrane/inactive degradation molecule complex; and exposing the membrane to an activating source, wherein following said exposing step, diffusion across the membrane of said eye improves. In a specific embodiment, the method further comprises administering to the individual a fluorescent molecule in an amount sufficient to associate with Bruch's membrane for visualization of the membrane. In a specific embodiment, the amount of fluorescence emitted is proportional to the amount of lipid or the amount of the altered protein in said Bruch's membrane. In another specific embodiment, the wavelength of the light required to excite the dye, the wavelength of the light emitted by the dye, or the lifetime of the dye is altered in a detectable fashion by the amount of lipid or altered protein in the Bruch's membrane. In an additional specific embodiment, the inactivated degradation molecule is administered in a pharmacologically acceptable composition.

In an additional embodiment of the present invention, there is a kit, housed in a suitable container, comprising an inactivated Bruch's membrane degradation molecule. In a specific embodiment, the kit further comprises an activating source for activation of said inactivated Bruch's membrane degrading molecule. In an additional specific embodiment, the kit further comprises a fluorescent molecule.

In some embodiments of the present invention, a targeted ocular tissue is visualized prior to and/or during activation of the inactive tissue-altering molecule. For example, Bruch's membrane may be visualized by delivery of a fluorescent molecule that targets Bruch's membrane; by detecting the autofluorescent signature from characteristic components of Bruch's membrane itself, which differentiates it from adjacent and surrounding tissues (by well-known means in the art); and/or by using OCT Doppler to identify the membrane's specific mechanical properties (also by well-known means in the art).

In another embodiment of the present invention, there is a method of diagnosing an eye disorder in at least one eye of an individual, comprising administering to the individual a fluorescent molecule in an amount sufficient for the fluorescent molecule to associate with Bruch's membrane in the eye; exposing Bruch's membrane with irradiation to view the fluorescence, wherein the quantity of fluorescence is an indicator of severity of the eye disorder. In a specific embodiment, the eye disorder is macular degeneration. In another specific embodiment, the irradiation is 2 photon irradiation.

In another embodiment of the present invention, there is a method of diagnosing an eye disorder in at least one eye of an individual, based on the intrinsic light scattering from targeted tissue such as Bruch's membrane. The technique of optical coherence tomography (OCT) with visible or infrared light is used to detect alterations in the physical or chemical nature of Bruch's membrane in the eye. OCT can be used to see not only the structure in the eye as has been used in some previous work on the human eye, but can also be used to study the mobility of the structures by Doppler OCT and the chemical nature by combining the OCT with an exogenous dye. In this embodiment, the OCT and/or its variants are used to determine the nature of the Bruch's membrane with altered properties to permit guided treatment. Treatment could be the photo-uncaging or photo-activation or photo-ablation of intrinsic or extrinsic substances in or near Bruch's membrane.

In an additional embodiment of the present invention, there is a method of treating an eye disorder of an individual, comprising administering to the individual a visualizing molecule in an amount sufficient to permit visualization of Bruch's membrane in the eye; administering to the individual an inactive form of a photoactive degradation molecule in an amount sufficient to form a Bruch's membrane/inactive photoactive degradation molecule complex; and exposing said complex to an activating source, wherein said activating source activates said inactive photoactive degradation molecule into an active form of said photoactive diffusion-enhancing molecule, said activation resulting in an increase in diffusion, alteration of composition, or both, across Bruch's membrane. In a specific embodiment, the visualization molecule is a fluorescent molecule. In another specific embodiment, the fluorescent molecule is joined to the inactive form of the photoactive molecule. In alternative embodiments, the membrane is visualized by its signature autofluorescent properties or by OCT Doppler methods. In an additional specific embodiment, the inactive photoactive molecule associates with a lipid in Bruch's membrane.

In one embodiment of the present invention, there is a method for altering an ocular tissue in an individual, comprising the steps of administering to the ocular tissue an inactive form of a tissue-altering molecule in an amount sufficient to target the molecule to the tissue; and exposing the molecule to an activating source, wherein the activating source activates the inactive tissue-altering molecule into an active form of the tissue-altering molecule, the activation resulting in alteration of at least part of the ocular tissue. In a specific embodiment, the method provides therapy for an eye disorder in said individual. In another specific embodiment, the eye disorder is age-related macular degeneration, juvenile macular degeneration, Sorby's fundus dystrophy, age-related decrease in visual function unrelated to macular degeneration, or glaucoma. In a specific embodiment, the inactive tissue-altering molecule is administered to the individual in a pharmacologically acceptable composition. In a further specific embodiment, the inactive tissue-altering molecule is administered in a pharmacologically acceptable composition systemically to the individual. In an additional specific embodiment, the inactive degradation molecule is administered in a pharmacologically acceptable composition to the individual orally, by injection, rectally, vaginally, or topically. If the administration is by injection, the injection may be intraocular or periocular, although other routes are acceptable.

In a specific embodiment, optical coherence tomography (OCT) is utilized for detection in the targeted tissues or cells, such as detection of changes in the composition (such as scattering or labeling with a specific agent) or the organization of the tissue, an example of which is Bruch's membrane. Doppler OCT provides informative information, such as that regarding motility of the scatterers in the targeted tissue and/or regarding targeting of the immobile area (such as the chemically altered area, etc.) for activating them with the uncaging agent.

The following numbered sentences in the form of claims define certain embodiments of the present disclosure:

1. A method of treating an eye disorder comprising the step of increasing diffusion across Bruch's membrane in said eye.

2. The method of claim 1, wherein the increased diffusion is a result of reducing the thickness, altering the composition, or both, of said membrane.

3. A method for increasing diffusion across Bruch's membrane in at least one eye of an individual, comprising the steps of:
   administering to the Bruch's membrane an inactive form of a diffusion-enhancing molecule in an amount sufficient to form a Bruch's membrane/inactive diffusion-enhancing molecule complex; and
   exposing said complex to an activating source, wherein said activating source activates said inactive diffusion-enhancing molecule into an active form of said diffusion-enhancing molecule, said activation resulting in an increase in diffusion across said membrane.

4. The method of claim 3, wherein the increase in diffusion is a result of reducing the thickness of the membrane, altering the composition of the membrane, or both.

5. The method of claim 3, wherein said increase in diffusion is a result of alteration in the membrane of a lipid, a protein, or both.

6. The method of claim 3, wherein the individual has an eye disorder.

7. The method of claim 6, wherein the eye disorder is age-related macular degeneration, juvenile macular degeneration, Sorby's fundus dystrophy, or age-related decrease in visual function unrelated to macular degeneration.

8. The method of claim 3, wherein the inactive diffusion-enhancing molecule binds directly to the membrane.

9. The method of claim 3, wherein the inactive diffusion-enhancing molecule is a protein, detergent, or surfactant.

10. The method of claim 9, wherein the protein is an enzyme.

11. The method of claim 10, wherein the inactive enzyme is further defined as being caged by at least one photo-removable protecting group on an amino acid sidechain of said enzyme.

12. The method of claim 11, wherein said protecting group is o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl, or a combination thereof.

13. The method of claim 11, wherein said protecting group is o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl, or derivatives thereof.

14. The method of claim 11, wherein the amino acid is cysteine, aspartate, glutamate, histidine, lysine, asparagine, glutamine, arginine, serine, threonine, tyrosine, or a combination thereof.

15. The method of claim 9, wherein the detergent is further defined as being caged by a compound comprising at least one o-nitrobenzyl, desyl, phenacyl, trans-o-cinnamoyl, coumarinyl, quinoline-2-onyl, xanthenyl, thioxanthenyl, selenoxanthenyl and anthracenyl, or stilbenyl group.

16. The method of claim 9, wherein the protein is further defined as being caged by an ultrasound contrast agent.

17. The method of claim 16, wherein the ultrasound contrast agent is a microbubble or a liposome.

18. The method of claim 9, wherein the protein further comprises a protein binding domain.

19. The method of claim 18, wherein the protein binding domain is a heterodimeric domain.

20. The method of claim 18, wherein the protein binding domain is a leucine zipper domain, a chitin-binding domain, or a Src homology 2 (SH2) domain.

21. The method of claim 3, wherein the inactive diffusion-enhancing molecule is administered to the individual in a pharmacologically acceptable composition.

22. The method of claim 21, wherein the inactive diffusion-enhancing molecule is administered in a pharmacologically acceptable composition systemically to the individual.

23. The method of claim 21, wherein the inactive diffusion-enhancing molecule is administered in a pharmacologically acceptable composition to the individual orally, by injection, rectally, vaginally, or topically.

24. The method of claim 23, wherein said injection is intraocular or periocular.

25. The method of claim 10, wherein said enzyme is a matrix metalloproteinase, a cholesterol esterase, a lipase, a cathepsin, a protease, or a combination thereof.

26. The method of claim 25, wherein the protease is a serine protease.

27. The method of claim 3, wherein said activating source is energy.

28. The method of claim 27, wherein said energy is light or ultrasound.

29. The method of claim 3, wherein said activating source is two-photon irradiation.

30. The method of claim 3, wherein said exposing step is further defined as exposing said complex to light energy from a focused laser source.

31. The method of claim 3, wherein the diffusion-enhancing molecule is labeled with a fluorescent molecule.

32. The method of claim 3, wherein said method further comprises the step of visualizing said membrane.

33. The method of claim 32, wherein said membrane visualizing is by delivery of a targeted fluorescent label for the membrane, by identification of the membrane's inherent autofluorescence, or by optical coherence tomography (OCT) Doppler.

34. A method of treating age-related macular degeneration in at least one eye of an individual, said macular degeneration characterized by a thickened Bruch's membrane, comprising:
   administering to said individual an inactivated diffusion-enhancing molecule in an amount sufficient for said molecule to associate with the membrane to form a Bruch's membrane/inactive diffusion-enhancing molecule complex, wherein said inactivated diffusion-enhancing molecule is administered in a pharmacologically acceptable composition; and
   exposing the membrane to an activating source, wherein following said exposing step, diffusion across the membrane of said eye improves.

35. The method of claim 34, wherein said Bruch's membrane is visualized.

36. The method of claim 35, wherein said visualizing is defined as administering to the individual a fluorescent molecule in an amount sufficient to associate with Bruch's membrane for visualization of the membrane.

37. The method of claim 35, wherein said visualizing is defined as identifying autofluorescence of the membrane.

38. The method of claim 35, wherein said visualizing is by optical coherence tomography (OCT) Doppler.

39. The method of claim 36, wherein the amount of fluorescence emitted is proportional to the amount of lipid in said Bruch's membrane.

40. The method of claim 35, wherein said visualizing is defined as administering to the individual visible or infrared light.

41. The method of claim 40, wherein said administering of visible or infrared light comprises using optical coherence tomography.

42. The method of claim 41, wherein said method further comprises administering an exogenous dye.

43. A kit, housed in a suitable container, comprising an inactivated Bruch's membrane diffusion-enhancing molecule.

44. The kit of claim 43, further comprising an activating source for activation of said inactivated Bruch's membrane degrading molecule.

45. The kit of claim 43, further comprising a fluorescent molecule.

46. A method of diagnosing an eye disorder in at least one eye of an individual, comprising:
   administering to the individual a fluorescent molecule in an amount sufficient for the fluorescent molecule to associate with Bruch's membrane in the eye;
   exposing Bruch's membrane with irradiation to view the fluorescence, wherein the quantity of fluorescence is an indicator of severity of the eye disorder.

47. The method of claim 46, wherein said method further comprises the step of visualizing said membrane.

48. The method of claim 47, wherein said membrane visualizing is by delivery of a targeted fluorescent label for the membrane, by identification of the membrane's inherent autofluorescence, or by optical coherence tomography (OCT) Doppler.

49. The method of claim 46, wherein the eye disorder is macular degeneration.

50. The method of claim 46, wherein the irradiation is 2 photon irradiation.

51. A method of treating an eye disorder of an individual, comprising:
   visualizing Bruch's membrane in the eye;
   administering to the individual an inactive form of a photoactive diffusion-enhancing molecule in an amount sufficient to form a Bruch's membrane/inactive photoactive diffusion-enhancing molecule complex; and
   exposing said complex to an activating source, wherein said activating source activates said inactive photoactive diffusion-enhancing molecule into an active form of said photoactive diffusion-enhancing molecule, said activation resulting in an increase in diffusion, alteration of composition, or both, across Bruch's membrane.

52. The method of claim 51, wherein said visualizing is by delivery of a targeted fluorescent label for the membrane, by identification of the membrane's inherent autofluorescence, or by optical coherence tomography (OCT) Doppler.

53. The method of claim 52, wherein the fluorescent label is joined to the inactive form of the photoactive molecule.

54. The method of claim 51, wherein the inactive photoactive molecule associates with a lipid in Bruch's membrane.

55. A method for altering an ocular tissue in an individual, comprising the steps of:
   administering to the ocular tissue an inactive form of a tissue-altering molecule in an amount sufficient to target said molecule to said tissue; and
   exposing said molecule to an activating source, wherein said activating source activates said inactive tissue-altering molecule into an active form of said tissue-altering molecule, said activation resulting in alteration of at least part of said ocular tissue.

56. The method of claim 55, wherein the method provides therapy for an eye disorder in said individual.

57. The method of claim 3, wherein said method further comprises the step of visualizing said tissue.

58. The method of claim 32, wherein said tissue visualizing is by delivery of a targeted fluorescent label for the tissue, by identification of the tissue's inherent autofluorescence, or by optical coherence tomography (OCT) Doppler.

59. The method of claim 56, wherein the eye disorder is age-related macular degeneration, juvenile macular degeneration, Sorby's fundus dystrophy, age-related decrease in visual function unrelated to macular degeneration, or glaucoma.

60. The method of claim 55, wherein the inactive tissue-altering molecule is administered to the individual in a pharmacologically acceptable composition.

61. The method of claim 55, wherein the inactive tissue-altering molecule is administered in a pharmacologically acceptable composition systemically to the individual.

62. The method of claim 55, wherein the inactive tissue-altering molecule is administered in a pharmacologically acceptable composition to the individual orally, by injection, rectally, vaginally, or topically.

63. The method of claim 62, wherein said injection is intraocular or periocular.

BRIEF DESCRIPTION OF THE FIGURES

FIG. 1 illustrates targeted photo-induced tissue alteration of Bruch's membrane lipids, in an exemplary embodiment of the present invention. It shows that following systemic administration, caged diffusion-enhancing molecules diffuse from the choriocapillaris into Bruch's membrane. Two-photon irradiation precisely deprotected the functional groups, and the diffusion-enhancing molecule is activated specifically within Bruch's membrane.

DESCRIPTION OF ILLUSTRATIVE EMBODIMENTS

It will be readily apparent to one skilled in the art that various substitutions and modifications may be made in the invention disclosed herein without departing from the scope and spirit of the invention.

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more.

The term "age-related macular degeneration (AMD)" as used herein is referred to as macular degeneration in an individual over the age of about 50. In one specific embodiment, it is associated with destruction and loss of the photoreceptors in the macula region of the retina resulting in decreased central vision and, in advanced cases, legal blindness. In specific embodiments, other degenerations are included in the scope of the term, such as Sorsby's fundus dystrophy.

The term "Bruch's membrane" as used herein refers to a five-layered structure separating the choriocapillaris from the RPE.

The term "caged" as used herein refers to the functional groups of a tissue-altering molecule being protected by another molecule/moiety. In a specific embodiment, the term refers to maintaining an inactive form of the tissue-alternating molecule, without an activating source.

The term "drusen" as used herein is defined as yellowish deposits located deep to the RPE in the inner aspect of Bruch's membrane.

The term "eye disorder" as used herein refers to a condition of having less than normal health related to at least one eye of an individual. In a preferred embodiment, the eye disorder comprises a thickened Bruch's membrane. In a specific embodiment, Bruch's membrane is thickened approximately twice its normal thickness. In other specific embodiments, the membrane is thickened about three times to ten times its normal thickness. Specific eye disorders in which Bruch's membrane is abnormally thickened include at least age-related macular degeneration, juvenile macular degeneration, Sorsby's fundus dystrophy, or normal aging with diminished capability to dark adapt. Other eye disorders may not be characterized by a thickened Bruch's membrane but may benefit through alteration of an ocular tissue, such as alteration of trabecular meshwork to increase outflow facility in glaucoma. Targeted tissue alteration using two photon irradiation can also be used to treat microvascular abnormalities in diabetic ocular disease, including diabetic macular edema and neovascularization. Selective two photon irradiation and uncaging of inactive drugs following systemic or local administration can be used to target drug effects to particular tissues in the eye. This form of selective uncaging can be used in extraocular tissues to achieve selective effects.

The term "macula" as used herein refers to the central area of the retina, including light-sensing cells of the central region of the retina.

The term "macular degeneration" as used herein refers to deterioration of the central portion of the retina, the macula.

The term "retina" as used herein refers to the neurological tissue at the posterior of the eye, containing the rods and cones that receive light and convert it to electrical signals for transmission via the optic nerve to the brain.

The term "tissue-altering agent" as used herein refers to at least one molecule that changes the physical, chemical, or both properties of a tissue. In a specific embodiment, the term refers to an agent that alters a tissue such that diffusion through or across is improved, at least partially. In other specific embodiments, the term refers to an agent that is capable of at least (that at least in part is undesirable) partially degrading components of a tissue. In additional specific embodiments, the term refers to an agent that is capable of reducing lipids and/or cross-linked proteins in a tissue, such as Bruch's membrane. In specific embodiments, the term regards degrading one or more of its components. In other specific embodiments, the tissue-altering molecule is a detergent that can extract lipidic and non-lipidic deposits from within a tissue such as Bruch's membrane.

The term "ultrasound contrast agent" as used herein refers to microstructures that can carry exogenous contrast agents. These microstructures can be disrupted by focused application of ultrasound irradiation. Examples include microbubbles (tiny gas bubbles, in suspension, that can strongly scatter ultrasound) or liposomes.

II. The Present Invention

The present invention is directed to the treatment of an eye disorder, particularly by effecting alteration of ocular tissue related to the disorder. This alteration may be of any kind, so long as the tissue is altered, but in particular embodiments it refers to enhancement of diffusion of a tissue using methods and compositions described herein. In a specific embodiment, the methods and compositions affect Bruch's membrane to improve an ocular disorder.

The eye disorder may be any kind, but in specific embodiments the eye disorder is AMD or other macular degenerations, such as Sorsby's fundus dystrophy, or any condition that results in thickening of the Bruch's membrane. In another specific embodiment, age related thickening even in the absence of macular degeneration is treated. The thickening in the elderly accounts for age related visual changes, such as difficulty in dark adaptation. Thus, the methods and compositions of the present invention are directed at changing the physical and/or chemical structure of an ocular tissue, and in specific embodiments the tissue is Bruch's membrane for the improvement of visual function in elderly patients with or without AMD (and non-elderly patients, such as in juvenile macular degeneration). In specific embodiments, the present invention is directed to the treatment of glaucoma with topical administration of at least one tissue-altering agent. Such treatment is useful for glaucoma, such as for the particular embodiment of alleviating a clogged trabecular meshwork in the pathogenesis of glaucoma.

In another specific embodiment, the present invention regards treatment for macular degeneration, either dry or wet. A skilled artisan recognizes that wet AMD may be treated with the methods of the present invention, given that after treatment of wet macular degeneration by currently known methods, the condition commonly recurs (recurrent choroidal neovascularization). In a further specific embodiment, the therapy described herein prevents such recurrences and may limit the extent (growth) of existing choroidal neovascularization, thus maintaining better vision. In specific embodiments of the present invention, by increasing nutritional delivery to the retina, the treatment causes regression of existing choroidal neovascularization.

Thus the present invention aims to treat eye disorders, such as macular degeneration, by focusing on the thickened Bruch's membrane associated with many eye disorders. This thickening is the result of abnormal deposition of lipid and cross-linked protein and precedes neovascularization through Bruch's membrane, followed by subsequent bleeding, leakage of serous fluid, and severe visual loss. As described herein, an improvement in diffusion across Bruch's membrane is achieved, thereby reducing the lipid and cross-linked protein barrier that accumulates in individuals with eye disorders, to prevent development of visual loss. In a specific embodiment, the chemical composition of the membrane is altered. For example, a detergent washes away lipids in the membrane. An enzyme degrades proteins within the membrane. In specific embodiments, the methods of the present invention result in an increase in hydraulic conductivity across Bruch's membrane and/or an increase in macromolecular and/or oxygen permeability of Bruch's membrane.

Generally, an individual with signs or symptoms of an aging Bruch's membrane is administered, such as systemically or locally, an inactive tissue-altering molecule. In some embodiments, the inactive molecules are visualizable prior to activation, such as by being fluorescent. Following sufficient time for adequate distribution of the inactive molecules, the molecules accumulate within multiple tissues, including Bruch's membrane. Once sufficient amounts are reached at Bruch's membrane, the visualizability of the molecules is used to precisely target Bruch's membrane with an energy source, such as light or ultrasound, that activates the tissue-altering molecules selectively.

In a specific embodiment, the present invention is useful for visualization of Bruch's membrane, such as for diagnostic techniques. That is, an inactive fluorescent compound is administered to an individual and associates with Bruch's membrane, such as by binding a lipid in Bruch's membrane. Energy, such as in the form of light, or more specifically 2 photon irradiation, is focused on the complex of inactive photoactive compound/Bruch's membrane, and the inactive photoactive compound is then activated. Energy emitted from the photoactive compound, such as light, allows visualization of Bruch's membrane. In specific embodiments, the amount of light emitted is proportional to the amount of lipid in Bruch's membrane. If the fluorescent molecule is incorporated into the caged tissue-altering agent, visualization of Bruch's membrane can be followed by activation of the degradative substance to effect controlled partial degradation of Bruch's membrane. In alternative embodiments, visualization occurs through the natural autofluorescent activity of constituents of Bruch's membrane and/or occurs through OCT Doppler methods.

III. Tissue-Altering Molecule

The present invention utilizes a tissue-altering molecule for delivery to an ocular tissue, in specific embodiments for treatment in the eye. The tissue-altering molecule may be diffusion-enhancing, degradative, or both, and it preferably alters the physical, chemical, or both properties of the tissue. A diffusion-enhancing molecule acts to increase diffusion across Bruch's membrane by either a) reducing the thickness of the membrane itself; and/or b) reducing the amount of deposits within Bruch's membrane, and/or by changing the chemical nature of Bruch's membrane. It is preferably inactive upon administration to the individual and active upon exposure to an energy source. In specific embodiments, the tissue-altering molecule is caged. In other specific embodiments, the tissue-altering molecule is a degradative enzyme, such as cholesterol esterases, lipases, matrix metalloproteinases, or any enzyme, or protein in particular, such as that can increase diffusion across Bruch's membrane, preferably by degrading one or more of its components. In other specific embodiments, the tissue-altering molecule is a detergent that can extract lipidic and non-lipidic deposits from within Bruch's membrane, which will increase diffusion across Bruch's membrane.

Some tissue-altering molecules comprise at least one amino acid residue and are in inactive form by caging, wherein at least one amino acid sidechain, such as from cysteine, aspartate, glutamate, histidine, lysine, asparagine, glutamine, arginine, serine, threonine, tyrosine, or a combination thereof, comprises a photo-removable protecting group, such as at least one coumarinyl, quinoline-2-onyl, xanthenyl, thioxanthenyl, selenoxanthenyl and anthracenyl, and/or stilbenyl group. In another embodiment, the tissue-altering molecule is inactivated through caging in an ultrasound contrast agent, such as microbubbles or liposomes. There are other tissue-alternating molecules without amino acid residues known in the art, such as surfactants.

The tissue-altering molecule is formulated so as to provide an effective concentration in the desired tissue. Although in some embodiments the tissue-altering molecule accumulates in non-affected tissue, this is not problematic for the individual, since precise targeting of the activating energy source to Bruch's membrane renders selective activation within the membrane. Other regions where the caged tissue-altering molecules accumulate are not treated with the activating energy; therefore, the caged tissue-altering molecules remain inactive and are eliminated via the kidneys and/or liver. In a specific embodiment, the caged molecule is not harmful or toxic in any manner and is nevertheless excreted from the body, preferably less than about 48 hours after administration, and more preferably less than about 24 hours after administration.

In some embodiments, the tissue-altering molecule is coupled to a specific binding ligand that may bind to a specific target molecule within Bruch's membrane. The target molecule may be endogenous to Bruch's membrane, or may be selectively delivered to Bruch's membrane by crosslinking the target molecule using 2-photon irradiation. In these embodiments, the tissue-altering molecule will be delivered in higher concentrations to the target tissue. In a specific embodiment, various protein-binding domains such as leucine zipper domains are associated with the tissue-altering molecule.

IV. Formulations

The tissue-altering molecule is formulated so as to provide an effective concentration in the desired tissue. Although in some embodiments the tissue-altering molecule accumulates in non-affected tissue, this is not problematic for the individual, since precise targeting of the activation energy source to Bruch's membrane renders selective activation within this tissue. Other regions where the caged tissue-altering molecules accumulate are not treated with the activating energy; therefore, the caged tissue-altering molecules remain inactive and are eliminated via the kidneys and/or liver. In some embodiments, the tissue-altering molecule is coupled to a specific binding ligand that may bind to a specific surface component of the target Bruch's membrane or, if desired, by formulation with a carrier that delivers higher concentrations to the target tissue. In a specific embodiment, various protein binding domains such as leucine zipper domains are associated with the tissue-altering molecule.

The nature of the formulation will depend in part on the mode of administration and on the nature of the selected degradation molecule. Any pharmaceutically acceptable excipient, or combination thereof, appropriate to the particular tissue-altering compound may be used. Thus, the compound may be administered as an aqueous composition, as a topical composition, as a transmucosal or transdermal composition, in an oral formulation or intravenous formulation, in a local injection (such as periocular or intraocular) or a combination thereof. The formulation may also include liposomes.

V. Administration and Dosage

The tissue-altering molecule compound can be administered in any of a wide variety of ways, for example, orally, parenterally, or rectally, or the compound may be placed directly in the eye, such as topically or by periocular injection. Parenteral administration, such as intravenous, intramuscular, or subcutaneous, is useful. Intravenous, periocular, and intraocular injection are particular embodiments for delivery of the present invention or components thereof.

The dose of tissue-altering molecule can vary widely depending on the mode of administration; the formulation in which it is carried, such as in the form of liposomes; or whether it is coupled to a target-specific ligand, such as an antibody or an immunologically active fragment. As is generally recognized, there is a nexus between the type of tissue-altering molecule, the formulation, the mode of administration, and the dosage level. Adjustment of these parameters to fit a particular combination is possible and routine.

VI. Energy Source

The energy source comprises any stimulus that renders an inactive tissue-altering molecule active. This preferably leads to activation of the inactive tissue-altering molecule. Although energy sources are well known in the art, exemplary forms of energy sources include light or ultrasound. In specific embodiments, 2-photon photochemistry is utilized. In a specific embodiment, monochromatic light is utilized.

The various parameters used for effective, selective photoactivation of the tissue-altering molecules in the invention are interrelated. Therefore, the dose should also be adjusted with respect to other parameters, for example, fluence, irradiance, duration of treatment, and time interval between administration of the dose and the therapeutic irradiation. All of these parameters should be adjusted to produce enhancement of visual function without significant damage to the ocular tissue, and a skilled artisan is well aware how to do so.

Compositions and methods related to two-photon absorption are well known in the art, although exemplary methods are described in U.S. Pat. No. 6,267,913, U.S. Pat. No. 6,472,541, and WO 00/31588, which are all incorporated by reference herein in their entirety.

VII. Generating Proteins Having Sidechains with Photo-Removable Protecting Groups Proteins may be caged using a number of strategies. Caging may be accomplished by treating the native, uncaged molecule with a reactive precursor to a caging group. For example, the sidechain of the amino acid cysteine may be caged with the photo-removable o-nitrobenzyl group by treating a cysteine-containing protein with o-nitrobenzylbromide. Alternative strategies for caging proteins include chemical synthesis of the protein using solid-phase peptide synthesis starting with the appropriate caged amino acids, by direct translational incorporation into proteins using methods based on nonsense suppression, or by supplementing auxotrophic strains of bacteria with the caged amino acids.

In a specific embodiment, a tissue-altering molecule is caged to render it inactive, prior to localization to Bruch's membrane and activation upon exposure to an energy source. In a specific embodiment, the tissue-altering molecule is a protein having amino acid side chains. Those amenable to modification with a protecting group, such as a photo-removable protecting groups, include cysteine, aspartate, glutamate, histidine, lysine, asparagine, glutamine, arginine, serine, threonine, or tyrosine. Examples of photo-removable protecting groups includes o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl, and/or derivatives thereof. These protecting groups are added to the side chains as described elsewhere herein.

VIII. Macular Degeneration

Light enters through the clear front surface of the eye (the cornea), passes through the opening of the pupil, through the lens and finally is perceived by the retina in the back of the eye. The retina is a multilayered structure that lines the inside of the globe. It is made up of specialized cells that convert the light to electrical impulses that travel to the brain and produce sight.

In the center of the retina, there is a tiny, extremely specialized area called the macula. It is approximately ⅛ inch in diameter-about the size of this letter "O". The macula has the most densely packed photoreceptors, which are cells that collect light. They consist of rods and cones, which also perceive color. The macula is supplied with oxygen-rich blood that nourishes the cells.

If the macula is intact, an individual sees the fine details of whatever is directly in front of him. Macular degeneration involves the deterioration or breakdown of this tiny structure. Central vision becomes blurred or disappears, and straight lines look wavy or broken. The edges of images are seen, but not what is in the middle of the image. In time, the sense of color is diminished because the cones are damaged. However, the patient does not experience total blindness, and there is almost always a ring of peripheral vision.

IX. Drusen

The primary characteristic of atrophic AMD is accumulation of macular drusen, a localized thickening of Bruch's membrane. Diffuse thickening of Bruch's membrane (basal linear deposit) is the best histopathologic predictor of choroidal neovascularization. The drusen are primarily comprised of vesicular material (lipids) and cross-linked protein The presence of drusen is a common characteristic of macular degeneration. In a specific embodiment, an individual having at least one eye with drusen or a thickened Bruch's membrane is treated with methods described herein.

EXAMPLES

The following examples are offered by way of example, and are not intended to limit the scope of the invention in any manner.

Example 1

Caged Tissue-Altering Molecules

Caged tissue-altering enzymes are constructed by masking various amino acid sidechains within the protein using photo-removable protecting groups. Examples of such groups are the o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl and derivatives thereof. These groups are introduced into the proteins by total chemical synthesis (including native chemical ligation), nonsense suppression methods, or post-translational modification. Based on the known matrix components of Bruch's membrane, cholesterol esterases, lipases, matrix metalloproteinases degrade portions of Bruch's membrane and improve trans-membrane diffusion. "Caging" these enzymes inactivates them. Thus, following systemic administration they circulate, bind to tissues and then are eliminated in their inactive form. Application of precisely focused light energy to Bruch's membrane (2-photon photochemistry) enables removal of the "cage protecting group" and selective activation of the enzyme(s) within Bruch's membrane. Once activated, controlled degradation takes place and trans-membrane diffusion is enhanced. This reduces the likelihood of developing choroidal neovascularization. It also may improve dark adaptation and night vision in elderly individuals with thickened Bruch's membrane. It also may cause regression of established choroidal neovascularization.

Alternatively, mild detergent molecules (e.g. surfactant) are "caged" using groups such as the o-nitrobenzyl, desyl, phenacyl, trans-o-cinnamoyl, coumarinyl, quinoline-2-onyl, xanthenyl, thioxanthenyl, selenoxanthenyl and anthracenyl, and/or stilbenyl moieties and their derivatives thereof and likewise activated by irradiation (for example, by 2-photon irradiation) to effect selective biochemical modification of Bruch's membrane. Similar to enzyme treatment, these activated detergent molecules alter the diffusion barrier of aged Bruch's membrane to lessen the likelihood of visual loss and/or improve visual function.

Example 2

Alternative Inactivation Embodiments

Degradative enzymes (matrix metalloproteinases, cholesterol esterases, lipases, serine proteases) can also be incorporated into ultrasound contrast agents such as microbubbles and liposomes. Carried within these contrast agents, the degradative molecules are inactive. Precise application of ultrasonic energy to Bruch's membrane causes cavitations of the contrast agent and release of the degradative enzymes into Bruch's membrane. Similar to the example above, enzymatic release improves trans-membrane diffusion and potentially improves visual function. Not activated by ultrasound, remaining extraocular encapsulated inactive enzymes are eliminated from the body without causing collateral tissue alterations.

Example 3

Targeting Improvements

Many of the enzymes administered in the previous examples are all present in Bruch's membrane and/or the RPE. Further, they are present in the circulation. To increase the local concentration of these enzymes within Bruch's membrane, these enzymes may be fused to various protein binding domains, such as a leucine zipper domain, a chitin-binding domain, or a Src homology 2 (SH2) domain. A skilled artisan recognizes that hetero-dimeric zippers consist of an acidic and a basic partner and may self assemble into coiled-coils that exist as dimers and higher order aggregates. Thus, in some embodiments, an acidic (basic) leucine zipper domain may be selectively delivered to Bruch's membrane via photo-crosslinking initiated by 2-photon irradiation. In specific embodiments, the enzyme is fused to a basic (acidic) leucine zipper domain and is administered, for example, systemically (such as orally or intravenously), or by injection (such as intraocular and/or periocular injection) and distributed to extracellular tissues, including Bruch's membrane. Formation of hetero-dimers within Bruch's membrane increases the local concentration of degradative enzymes and subsequently enhances trans-membrane diffusion properties. Because the concentration of these degradative enzymes will remain low in other tissues, there are no undesired collateral tissue alterations. Additionally, enzymes may be produced containing photo-active groups (such as the benzophenoyl, phenylazide, trifluromethylphenyldiazirinyl, and derivatives thereof) using the methods outlined in Example 1. Systemic administration of such enzymes, followed by selective irradiation of Bruch's membrane initiates photo-crosslinking between the enzymes and Bruch's membrane, increasing the concentrations of the degradative enzymes. In other embodiments, the protein-binding domains facilitate association of a targeting tissue-altering molecule with the tissue to be targeted, such as by binding to proteins on or within the tissue.

Example 4

Treatment of Ocular Disorder

A patient with an ocular disorder, such as atrophic age-related macular degeneration (in exemplary embodiments), is administered a caged, inactivated enzyme capable of altering Bruch's membrane upon photoactivation. In specific embodiments, the administration is systemic (such as intravenously or orally), or by injection (such as intraocular and/or periocular injection). In other specific embodiments, the caged, inactivated enzyme is labeled, such as fluorescently labeled, although in alternative embodiments the caged, inactivated enzyme is not labeled.

For illustrative purposes only, the caged, inactivated molecule is fluorescent. Several minutes following administration, the fluorescent, caged degradative complex is viewed in macular Bruch's membrane by 2 photon irradiation. After focusing on the fluorescent label in macular Bruch's membrane, a higher dose of 2 photon irradiation is applied to uncage the enzyme and initiate partial degradation of Bruch's membrane. Systemically distributed non-irradiated caged enzyme is excreted in its inactive form. Two photon irradiation viewing of labeled Bruch's membrane and photoactivation of the degradative substance are both performed at levels non-toxic to ocular structures.

Alternatively, a fluorescent label not attached to the caged degradative enzyme complex is administered systemically. About ten to sixty minutes later, the caged degradative molecular complex is administered. About five minutes later, Bruch's membrane is visualized by 2 photon irradiation of the fluorescent label. A higher dose of 2 photon irradiation is then used to activate the caged degradative molecular complex.

In another embodiment, a fluorescent label not attached to the caged degradative enzyme complex is administered systemically. About ten to sixty minutes later, 2 photon irradiation is used to visualize the quantity of fluorescence in Bruch's membrane. Quantification of fluorescence is a diagnostic indicator of severity of atrophic macular degeneration.

In another embodiment of the present invention, there is a method of identifying a tissue to be treated based on the intrinsic light scattering from targeted tissue such as Bruch's membrane. Optical coherence tomography (OCT) with visible or infrared light is used to detect alterations in the physical or chemical nature of Bruch's membrane in the eye. OCT can be used to see not only the structure in the eye but also the mobility of the structures by Doppler OCT and the chemical nature by combining the OCT with an exogenous dye. In this embodiment, the OCT and/or its variants are used to determine the nature of the Bruch's membrane with altered properties to permit guided treatment. Treatment could be the photo-uncaging or photo-activation or photo-ablation of intrinsic or extrinsic substances in or near Bruch's membrane.

An exemplary embodiment targeting Bruch's membrane is depicted in FIG. 1.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference herein.

U.S. Pat. No. 5,756,541
U.S. Pat. No. 5,798,349
U.S. Pat. No. 5,910,510
U.S. Pat. No. 5,935,942
U.S. Pat. No. 6,128,525
U.S. Pat. No. 6,140,314
U.S. Pat. No. 6,225,303
U.S. Pat. No. 6,248,727
U.S. Pat. No. 6,267,913
U.S. Pat. No. 6,472,541
WO 00/31588

We claim:

1. A method for increasing diffusion across Bruch's membrane in at least one eye of an individual, comprising the steps of:

administering to the Bruch's membrane an inactive form of a diffusion-enhancing molecule in an amount sufficient to form a Bruch's membrane/inactive diffusion-enhancing molecule complex; and exposing said complex to an activating source, wherein said activating source activates said inactive diffusion-enhancing molecule into an active form of said diffusion-enhancing molecule, said activation resulting in an increase in diffusion across said membrane.

2. The method of claim 1, wherein the diffusion-enhancing molecule comprises a surfactant caged by at least one photo-removable protecting group.

3. The method of claim 2, wherein the protecting group is an o-nitrobenzyl, a desyl, a phenacyl, a trans-o-cinnamoyl, a coumarinyl, a quinoline-2-onyl, a xanthenyl, a thioxanthenyl, a selenoxanthenyl, an anthracenyl, or a stilbenyl group.

4. The method of claim 1, wherein the administering comprises orally administering, injecting, rectally administering, vaginally administering, or topically administering the diffusion-enhancing molecule to the individual.

5. The method of claim 4, wherein the injecting comprises intraocularly injecting the diffusion-enhancing molecule to the individual.

6. The method of claim 4, wherein the injecting comprises periocularly injecting the diffusion-enhancing molecule to the individual.

7. The method of claim 1, wherein the activating source comprises light energy.

8. The method of claim 7, wherein the light energy comprises two-photon irradiation.

9. The method of claim 1, further comprising visualizing the Bruch's membrane by delivery of a targeted fluorescent label to the Bruch's membrane, by identification of the inherent autofluorescence of the Bruch's membrane, or by optical coherence tomography (OCT) Doppler.

10. A method of treating age-related macular degeneration in at least one eye of an individual, said macular degeneration characterized by a thickened Bruch's membrane, comprising:
administering to said individual an inactivated diffusion-enhancing molecule in an amount sufficient for said molecule to associate with the Bruch's membrane to form a Bruch's membrane/inactive diffusion-enhancing molecule complex, wherein said inactivated diffusion-enhancing molecule is administered in a pharmacologically acceptable composition; and
exposing the complex to an activating source, wherein following said exposing step, diffusion across the Bruch's membrane of said eye improves.

11. The method of claim 10, wherein the diffusion-enhancing molecule comprises a surfactant caged by at least one photo-removable protecting group.

12. The method of claim 11, wherein the protecting group is an o-nitrobenzyl, a desyl, a phenacyl, a trans-o-cinnamoyl, a coumarinyl, a quinoline-2-onyl, a xanthenyl, a thioxanthenyl, a selenoxanthenyl, an anthracenyl, or a stilbenyl group.

13. The method of claim 10, wherein the administering comprises orally administering, injecting, rectally administering, vaginally administering, or topically administering the diffusion-enhancing molecule to the individual.

14. The method of claim 13, wherein the injecting comprises intraocularly injecting the diffusion-enhancing molecule to the individual.

15. The method of claim 13, wherein the injecting comprises periocularly injecting the diffusion-enhancing molecule to the individual.

16. The method of claim 10, wherein the activating source comprises light energy.

17. The method of claim 16, wherein the light energy comprises two-photon irradiation.

18. The method of claim 10, further comprising visualizing the Bruch's membrane by delivery of a targeted fluorescent label to the Bruch's membrane, by identification of the inherent autofluorescence of the Bruch's membrane, or by optical coherence tomography (OCT) Doppler.

19. A method of treating an eye disorder of an individual, comprising:
visualizing Bruch's membrane in the eye;
administering to the individual an inactive form of a photoactive diffusion-enhancing molecule in an amount sufficient to form a Bruch's membrane/inactive photoactive diffusion-enhancing molecule complex; and
exposing said complex to an activating source, wherein said activating source activates said inactive photoactive diffusion-enhancing molecule into an active form of said photoactive diffusion-enhancing molecule, said activation resulting in an increase in diffusion, alteration of composition, or both, across Bruch's membrane.

20. The method of claim 19, wherein the diffusion-enhancing molecule comprises a surfactant caged by at least one photo-removable protecting group.

21. The method of claim 20, wherein the protecting group is an o-nitrobenzyl, a desyl, a phenacyl, a trans-o-cinnamoyl, a coumarinyl, a quinoline-2-onyl, a xanthenyl, a thioxanthenyl, a selenoxanthenyl, an anthracenyl, or a stilbenyl group.

22. The method of claim 19, wherein the administering comprises orally administering, injecting, rectally administering, vaginally administering, or topically administering the diffusion-enhancing molecule to the individual.

23. The method of claim 22, wherein the injecting comprises intraocularly injecting the diffusion-enhancing molecule to the individual.

24. The method of claim 22, wherein the injecting comprises periocularly injecting the diffusion-enhancing molecule to the individual.

25. The method of claim 19, wherein the activating source comprises light energy.

26. The method of claim 25, wherein the light energy comprises two-photon irradiation.

27. The method of claim 19, wherein the visualizing comprises delivering a targeted fluorescent label to the Bruch's membrane, identifying the inherent autofluorescence of the Bruch's membrane, or visualizing the Bruch's membrane by optical coherence tomography (OCT) Doppler.

28. A method for altering an ocular tissue in an individual, comprising the steps of:
administering to the ocular tissue a pharmacologically acceptable composition comprising an inactive form of a tissue-altering molecule in an amount sufficient to form a Bruch's membrane/inactive tissue-altering molecule complex; and
exposing said complex to an activating source, wherein said activating source activates said inactive tissue-altering molecule into an active form of said tissue-altering molecule, said activation resulting in alteration of at least part of said Bruch's membrane.

29. The method of claim 28, wherein the tissue-altering molecule comprises a surfactant caged by at least one photo-removable protecting group.

30. The method of claim 29, wherein the protecting group is an o-nitrobenzyl, a desyl, a phenacyl, a trans-o-cinnamoyl, a coumarinyl, a quinoline-2-onyl, a xanthenyl, a thioxanthenyl, a selenoxanthenyl, an anthracenyl, or a stilbenyl group.

31. The method of claim 28, wherein the administering comprises orally administering, injecting, rectally administering, vaginally administering, or topically administering the diffusion-enhancing molecule to the individual.

32. The method of claim 31, wherein the injecting comprises intraocularly injecting the diffusion-enhancing molecule to the individual.

33. The method of claim 31, wherein the injecting comprises periocularly injecting the diffusion-enhancing molecule to the individual.

34. The method of claim 28, wherein the activating source comprises light energy.

35. The method of claim 34, wherein the light energy comprises two-photon irradiation.

36. The method of claim 28, further comprising visualizing the Bruch's membrane by delivery of a targeted fluorescent label to the Bruch's membrane, by identification of the inherent autofluorescence of the Bruch's membrane, or by optical coherence tomography (OCT) Doppler.

* * * * *